US008791110B2

(12) United States Patent
Amberg et al.

(10) Patent No.: US 8,791,110 B2
(45) Date of Patent: Jul. 29, 2014

(54) ANTI-ARENAVIRAL COMPOUNDS

(75) Inventors: Sean M. Amberg, Corvallis, OR (US); Dongcheng Dai, Corvallis, OR (US); Tove C. Bolken, Keizer, OR (US); Dennis E. Hruby, Albany, OR (US)

(73) Assignee: Siga Technologies, Inc., Corvallis, OR (US)

( * ) Notice: Subject to any disclaimer, the term of this patent is extended or adjusted under 35 U.S.C. 154(b) by 270 days.

(21) Appl. No.: 13/339,478

(22) Filed: Dec. 29, 2011

(65) Prior Publication Data

US 2012/0308519 A1 Dec. 6, 2012

Related U.S. Application Data

(63) Continuation-in-part of application No. 12/162,395, filed as application No. PCT/US2007/002570 on Jan. 31, 2007, now Pat. No. 8,106,058.

(60) Provisional application No. 60/763,921, filed on Feb. 1, 2006.

(51) Int. Cl.

| | |
|---|---|
| ***A61K 31/535*** | (2006.01) |
| ***A61K 31/497*** | (2006.01) |
| ***A61K 31/501*** | (2006.01) |
| ***A61K 31/445*** | (2006.01) |
| ***A61K 31/17*** | (2006.01) |

(52) U.S. Cl.

USPC .............. 514/231.2; 514/252.12; 514/253.01; 514/317; 514/580

(58) Field of Classification Search

USPC ............. 514/231.2, 252.12, 253.01, 317, 580

See application file for complete search history.

(56) References Cited

U.S. PATENT DOCUMENTS

| | | | | |
|---|---|---|---|---|
| 2,913,322 | A * | 11/1959 | Beaver et al. | 504/226 |
| 7,687,641 | B2 | 3/2010 | Jordan et al. | |
| 2002/0111378 | A1 | 8/2002 | Stamos et al. | |
| 2007/0254934 | A1 | 11/2007 | Hruby | |
| 2007/0287735 | A1 | 12/2007 | Jordan et al. | |
| 2008/0300265 | A1 | 12/2008 | Hruby | |
| 2009/0036513 | A1 | 2/2009 | Hruby | |
| 2009/0180980 | A1 | 7/2009 | Hruby | |
| 2009/0203675 | A1 | 8/2009 | Deng et al. | |

FOREIGN PATENT DOCUMENTS

| | | | |
|---|---|---|---|
| CA | 2633400 | A1 | 6/2007 |
| JP | 2009-519265 | A | 5/2009 |
| WO | WO2004099179 | A1 | 11/2004 |
| WO | WO 2005037257 | | 4/2005 |
| WO | WO 2006/062898 | | 6/2006 |
| WO | WO2006062898 | A2 | 6/2006 |
| WO | WO2007068380 | A1 | 6/2007 |
| WO | WO2007068380 | A1 | 8/2007 |
| WO | WO 2007/103111 | | 9/2007 |
| WO | WO 2007/120374 | | 10/2007 |
| WO | WO2008079159 | A2 | 7/2008 |
| WO | WO 2007/100888 | | 9/2008 |
| WO | WO2008130348 | A1 | 10/2008 |
| WO | WO 2008147474 | | 12/2008 |
| WO | WO2008147474 | A2 | 12/2008 |
| WO | WO2008147962 | A1 | 12/2008 |
| WO | WO2009029622 | A2 | 3/2009 |
| WO | WO2009123776 | A2 | 10/2009 |
| WO | WO2009149054 | A1 | 12/2009 |

OTHER PUBLICATIONS

Beaver et al. "The preparation and bacteriostatic activity of substituted Urea," Journal of the American Chemical Society, 1957, vol. 79, pp. 1236-1245.*

Wen et al. "Piperazine. I. Synthesis of alkyl 1-methylpiperazine-4-dithiocarbamate citrates and 1-methyl-4-(arylthiocarbamyl)piperazine citrates," Huaxue Xuebao, 1956, vol. 22, pp. 379-385, CAPLUS abstract. AN 1958:61237.*

Yoshizumi et al. "Synthesis and structure-Activity relationships of Novel phenylcyanoguanidine derivatives as potassium channel openers," Chem. Pharm. Bull. 1996, vol. 44, No. 11, pp. 2042-2050.*

Broken et al. Identificaton and characterization of potent small molecule inhibitor of hemorrhagic fever new world arenaviruses. Antiviral Research, Mar. 2005, vol. 65.

Golf et al. A survey of antiviral drugs for bloweapons, Antiviral Chemistry and Chemotherapy, 2005, vol. 16, pp. 283-294.

Nanden Prasad R. et al., "Potential Antihypertensive Agents. IV. Unsymmetrically 1, 4-Disubstituted Piperazines. II" J. Medicinal Chem., vol. 12, No. 3, May 1969, pp. 551-552.

Pandey B.R. et al., "4 Arylaminothiocarbonyl-1-D-Methoxyphenyic Arbamidoethyl Piperazines as Anti Convulsants", Journal of Heterocyclic Chemistry, vol. 17, No. 5, 1980, pp. 1119-1120.

European Search Report, Application No. 07 76 9434, Dated Jun. 9, 2011.

Co-pending U.S. Appl. No. 12/673,983 ; Inventor Dai et al.; filed Feb. 18, 2010.

* cited by examiner

*Primary Examiner* — Shengjun Wang

(74) *Attorney, Agent, or Firm* — Charles C. Achkar; Ostrolenk Faber LLP

(57) ABSTRACT

Described herein are 4-methyl-piperazine-1-carbothioic acid amide derivatives and analogs, as well as compositions containing the same, for the treatment or prophylaxis of viral infections and diseases associated therewith, particularly those viral infections and associated diseases caused by hemorrhagic fever viruses, such as Arenaviruses.

6 Claims, No Drawings

ANTI-ARENAVIRAL COMPOUNDS

CROSS REFERENCE TO RELATED APPLICATIONS

This application is a continuation-in-part and claims priority to U.S. patent application Ser. No. 12/162,395, filed Nov. 4, 2008, which is a national stage entry of PCT/US07/02570, filed on Jan. 31, 2007, which claims priority to U.S. Provisional Application Ser. No. 60/763,921, filed on Feb. 1, 2006. All the applications are incorporated herein by reference in the entirety and for all purposes.

STATEMENT REGARDING FEDERALLY SPONSORED RESEARCH OR DEVELOPMENT

This invention was made with U.S. government support under Grant No. 1R43A1056525-01 awarded by the National Institute of Health (NIH). The U.S. Government has certain rights in the invention.

FIELD

Described herein are 4-methyl-piperazine-1-carbothioic acid amide derivatives and analogs, as well as compositions containing the same, for the treatment or prophylaxis of viral infections and diseases associated therewith, particularly those viral infections and associated diseases caused by hemorrhagic fever viruses, such as Arenaviruses.

BACKGROUND

The family Arenaviridae consists of a single genus (Arenavirus) that includes several viruses. Rodents are the primary reservoirs of Arenaviruses, and human infection is thought to occur by contact with infectious rodent excreta. Two groups of Arenaviruses are currently recognized. The Old World group (lymphocytic choriomeningitis (LCM)-Lassa complex) includes viruses indigenous to Africa and the ubiquitous LCM virus. The New World group (Tacaribe complex) includes viruses indigenous to the Americas. Several Arenaviruses are associated with severe hemorrhagic disease in humans. Lassa virus (from the Old World group) is responsible for Lassa hemorrhagic fever, while four viruses from the New World group (all from Clade B) cause severe hemorrhagic fever in humans. Those viruses are Junín virus, which is responsible for Argentine hemorrhagic fever; Machupo virus, which is responsible for Bolivian hemorrhagic fever; Guanarito virus, which is responsible for Venezuelan hemorrhagic fever; and Sabiá virus, which was isolated from a fatal case of hemorrhagic fever in Brazil. It is estimated that Lassa virus causes 100,000-300,000 infections and approximately 5,000 deaths annually. So far an estimated 30,000 confirmed cases of Junín infections have been documented, while about 2,000 of Machupo, 200 of Guanarito and only 2 of Sabiá.

Recent concerns over the use of Arenaviruses as biological weapons have underscored the necessity of developing small-molecule therapeutics that target these viruses. These Arenaviruses are a serious biowarfare threat because of: (i) their high disease morbidity and mortality (case fatality rates of 15-30%); (ii) their ease of dissemination and aerosol transmissibility; and (iii) the ease of obtaining and producing large quantities of these viruses.

Currently, there are no specific treatments approved for use against Arenavirus hemorrhagic fevers. Present disease management consists of general supportive care—monitoring and correcting fluid, electrolyte and osmotic imbalances and treating hemorrhage with clotting factor or platelet replacement. Convalescent immune serum therapy may be effective in treating cases of Junín and Machupo virus disease, but the availability of such serum is extremely limited.

Ribavirin, a nucleoside analog, has been used with some success in Lassa fever patients. In small trials, intravenous ribavirin given to patients within the first 6 days after development of fever decreased mortality from 76% to 9%. A controlled trial of 18 patients with Argentine hemorrhagic fever resulted in 13% mortality in treated patients, compared with 40% mortality in untreated patients. However, Ribavirin therapy is associated with adverse effects, including a dose-related, reversible hemolytic anemia, and also has demonstrated teratogenicity and embryo lethality in several animal species. It is therefore classified as a pregnancy category X drug, contraindicated during pregnancy. Intravenous ribavirin is available in limited supplies in the U.S. for compassionate use under an IND application. The dosing regimen for ribavirin therapy that has been used in cases of Lassa fever consists of an initial 30 mg/kg intravenous (IV) loading dose, followed by 16 mg/kg IV every 6 hours for 4 days; then 8 mg/kg IV every 8 hours for 6 days (total treatment time 10 days). The cost of treatment for an adult male is approximately $800. The attributes of ribavirin make it less than ideal for the treatment of Arenavirus hemorrhagic fevers.

A number of in vitro inhibitors of Arenavirus replication have been reported in the literature including phenothiazines, trifluoroperazine and chlorpromazine amantadine brassinosteroids, and actinomycin D. The anti-Arenavirus activities of these compounds are generally weak and non-specific.

The only Arenavirus hemorrhagic fever for which studies have been undertaken toward development of a vaccine has been Argentine hemorrhagic fever (AHF) caused by Junín virus. A live-attenuated vaccine, called Candid 1, has been evaluated in controlled trials among agricultural workers in AHF-endemic areas, where it appeared to reduce the number of reported AHF cases with no serious side effects. It is not known if the Candid 1 vaccine would be useful against other Arenavirus hemorrhagic fevers and this vaccine is not available in the United States of America.

Based on these data, new therapies and preventives are clearly needed for infections and diseases caused by Arenavirus infection.

All human pathogenic Arenaviruses from the New World group causing hemorrhagic fever are from the Clade B. These human pathogen viruses require manipulation under high-level containment (BSL-4). However, Amapari and Tacaribe viruses, which are also from Clade B, can be grown in tissue culture under BSL-2 (low-level) containment. Working under low-level containment makes experimentation easier and safer with these viruses. While Amapari virus produces low cytopathic effect, Tacaribe virus can be grown readily in cell culture and produce robust CPE in 4 to 6 days. Since this CPE is directly related to viral replication, compounds that inhibit virus replication in cell culture can be identified readily as conferring protection from virus-induced CPE (although it is theoretically possible to inhibit CPE without inhibiting virus replication). Moreover, compounds having identified activity against Tacaribe virus will also likely be active against Arenavirus human pathogen causing hemorrhagic fever (Junín, Machupo, Guanarito and Sabiá) given the high degree of homology (around 70% identity for all 4 proteins of Tacaribe virus compared to Junín virus, with long stretch of protein with perfect identity) between these viruses.

SUMMARY

The present invention provides for compounds, compositions, and methods for treatment of an Arenavirus infection, as well as diseases associated therewith.

In one embodiment, the invention relates to a method for treatment of an Arenavirus infection that comprises administering in a therapeutically effective amount to a mammal in need thereof a compound of Formula I or a pharmaceutically acceptable salt thereof.

In another embodiment, the invention relates to a pharmaceutical composition that comprises a pharmaceutically-effective amount of the compound of Formula I or a pharmaceutically-acceptable salt thereof, and a pharmaceutically-acceptable carrier.

The compounds of Formula I are described below:

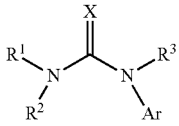

wherein $R^1$, $R^2$ and $R^3$ are independently hydrogen, alkyl, alkenyl, alkynyl, or unsubstituted or substituted cycloalkyl, arylalkyl, aryl, or $R^1$ and $R^2$ together may form a substituted or unsubstituted ring, which may include one or more heteroatoms in the ring;

X is O or S; and

Ar is substituted or unsubstituted aryl or heteroaryl, said cycloalkyl, arylalkyl, and aryl group substituents being one or more radical(s) independently selected from the group consisting of a straight- or branched chain alkyl, alkoxy, alkoxyalkyl, alkoxyalkoxy, halogen, polyfluoroalkyl, polyfluoroalkoxy, carboxy, cyano, nitro, amido, amidoalkyl, carboxamide, alkylthio, alkylsulfinyl, alkylsulfonyl, sulfonamide, and mercapto;

or a pharmaceutically acceptable salt thereof.

DETAILED DESCRIPTION

The present invention provides for compositions, compounds and methods for the treatment of hemorrhagic fever viruses, such as Arenaviruses. However, prior to providing further detail, the following terms will first be defined.

DEFINITIONS

The compounds described herein are, collectively, the compounds of Formula I, pharmaceutically acceptable salts thereof, their isomers, and mixtures thereof. Compounds are identified herein by their chemical structures and/or chemical names. Where a compound is referred to by both a chemical structure and a chemical name, and that chemical structure and chemical name conflict, the chemical structure is determinative of the compound's identity.

The term "living host" as used herein refers to an organism that is living and capable of being infected with a virus, such as an arenavirus; for example, a mammal, which includes a human.

The term "alkyl" as used herein refers to straight or branched chain aliphatic hydrocarbon radicals of 1 to 4 carbon atoms, optionally up to 6 carbon atoms or as high as 10 or more carbon atoms. Similarly, the term "alkyl", or any variation thereof, used in combination form to name substituents, such as alkoxy (—O-alkyl), alkylthio (—S-alkyl), monoalkylamino (—NH-alkyl), dialkylamino, (—N-(alkyl)alkyl), alkylsulfonyl (—$S(O)_2$-alkyl), carboxyalkyl (-alkyl-COOH), or the like, also refers to aliphatic hydrocarbon radicals of one to four carbon atoms, optionally one to six carbon atoms. Also "alk" in structural formula denotes an alkyl group, unless divalency is indicated in which case the "alk" denotes the corresponding alkylene group(s). Additionally, the term "lower alkyl" denotes an alkyl group having one to four carbon atoms.

The term "alkenyl" as used herein refers to straight or branched chain aliphatic hydrocarbon radicals of 2 to 7 carbon atoms containing one double bond. Such alkenyl moieties may exist in the E or Z configurations; the compounds described herein include both configurations. The term "alkynyl" as used herein refers to straight or branched chain aliphatic hydrocarbon radicals containing 2 to 7 carbon atoms having at least one triple bond.

The term "phenyl" as used herein refers to a group. A "substituted phenyl" refers to a phenyl group that is substituted with the indicated substituents.

As used herein, the term "aryl", when used as such, refers to an aromatic carbocyclic group, having 6 to 10 carbon atoms including without limitation phenyl and napthyl.

The term "heteroaryl," as used herein, refers to a 5- or 6-membered aromatic cyclic group having at least one carbon atom and one or more oxygen, nitrogen or sulfur atoms in the ring, as for example furyl, thienyl, pyridyl, pyrrolyl, oxazolyl, thiazolyl, imidazolyl, pyrazolyl, isoxazolyl, isothiazolyl, 1,2,3-oxadiazolyl, 1,2,3-triazolyl, tetrazolyl, and the like, including all position isomers. Suitable heteroaryl groups include, but are not limited to, pyridine, thiazole and thiophene.

As used herein, the term "cycloalkyl" refers to a saturated hydrocarbon ring. Cycloalkyls can be monocyclic or can be fused, spiro or bridged bicyclic or tricyclic ring systems. Monocyclic cycloalkyl rings contain from 3 to 7 carbon atoms, optionally from 3 to 10 carbon atoms, as for example cyclopropyl, cyclobutyl, cyclopentyl, and cyclohexyl. Bicyclic and tricyclic cycloalkyl rings contain from 7 to 19 carbon atoms, optionally from 7 to 28 carbon atoms, in the ring system; and include, for example, adamantyl, bicyclo[2.2.1]heptyl, bicyclo[2.2.2]cyclooctanyl, tricyclo[3.2.2.02,4]nonyl, and norbornyl, and bicyclo[3.2.2]nonyl. As used herein, the term "cycloalkenyl" refers to an unsaturated hydrocarbon ring. Cycloalkenyl rings are non-aromatic and contain one or more carbon-carbon double bonds. Cycloalkenyl rings are monocyclic, or are fused, spiro or bridged bicyclic or tricyclic ring systems. Monocyclic cycloalkenyl rings contain from 5 to 7 carbon atoms, optionally from 5 to 10 carbon atoms, and include, for example, cyclopropenyl, cyclobutenyl, cyclopentenyl, and cyclohexenyl. Bicyclic and tricyclic cycloalkenyl rings contain from 7 to 19 carbon atoms in the ring, optionally from 7 to 28 carbon atoms, in the ring system; and include, for example, bicyclo[2.2.1]hept-2-ene, bicyclo[2.2.2]cyclooct-2-enyl, tricyclo[3.2.2.02,4]non-6-enyl, and bicyclo[3.2.2]non-6-enyl.

The term "amido," as used herein, refers to a radical or substituent of the formula —NR"C(═O)R"', wherein R" and R"' represent hydrogen or alkyl.

The term "carboxamide," as used herein, refers to a radical or substituent of the formula —C(═O)—NR"R"', wherein R" and R"' are as previously defined.

The term "sulfonamide," as used herein, refers to a radical or substituent of the formula —$SO_2$NR"R"' or —NR"$SO_2$R"', wherein R" and R"' are as previously defined.

The term "halogen," as used herein, refers to a radical or substituent selected from the group consisting of chloro, bromo, iodo, and fluoro.

The term "HPLC," as used herein, refers to high-performance liquid chromatography.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is an oxo (=O) group, then 2 hydrogens on the atom are replaced.

Compounds described herein are also useful in preventing or resolving arena viral infections in cell, tissue or organ cultures and other in vitro applications. For example, inclusion of compounds described herein as a supplement in cell or tissue culture growth media and cell or tissue culture components will prevent viral infections or contaminations of cultures not previously infected with viruses. Compounds described above may also be used to eliminate or attenuate viral replication in cultures or other biological materials infected or contaminated with viruses (for example, blood), after a suitable treatment period, under any number of treatment conditions as determined by the skilled artisan.

The compounds described herein can form useful salts with inorganic and organic acids such as hydrochloric, sulfuric, acetic, lactic, or the like and with inorganic or organic bases such as sodium or potassium hydroxide, piperidine, ammonium hydroxide, or the like. The pharmaceutically acceptable salts of the compounds of Formula 1 are prepared following procedures that are familiar to those skilled in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The present invention relates to a method for treatment of an Arenavirus infection that comprises administering in a therapeutically effective amount to a mammal in need thereof, a compound of Formula I below:

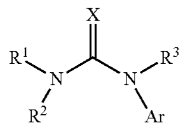

wherein $R^1$, $R^2$ and $R^3$ are independently hydrogen, alkyl, alkenyl, alkynyl, or unsubstituted or substituted cycloalkyl, arylalkyl, aryl, or $R^1$ and $R^2$ together may form a substituted or unsubstituted ring, which may include one or more heteroatoms in the ring;

X is O or S; and

Ar is substituted or unsubstituted aryl or heteroaryl, said cycloalkyl, arylalkyl, and aryl group substituents being one or more radical(s) independently selected from the group consisting of a straight- or branched chain alkyl, alkoxy, alkoxyalkyl, alkoxyalkoxy, halogen, polyfluoroalkyl, polyfluoroalkoxy, carboxy, cyano, nitro, amido, amidoalkyl, carboxamide, alkylthio, alkylsulfinyl, alkylsulfonyl, sulfonamide, and mercapto; and wherein compound of Formula I is selected from the group consisting of:

N1,N4-diphenylpiperazine-1,4-dicarbothioamide;

N-(4-chlorophenyl)-4-methyl-piperazine-1-carbothioamide;

N-(3,4-dichlorophenyl)-4-phenyl-piperazine-1-carbothioamide;

N-(3-chlorophenyl)-4-methyl-piperazine-1-carbothioamide;

N-(2,4-dichlorophenyl)-4-methyl-piperazine-1-carbothioamide;

4-methyl-N-(m-tolyl)piperazine-1-carbothioamide;

N-(3,4-dichlorophenyl)piperidine-1-carbothioamide;

N-(3,4-dichlorophenyl)morpholine-4-carbothioamide;

4-methyl-N-[3-(trifluoromethyl)phenyl]piperazine-1-carbothioamide;

ethyl 4-[(3,4-dichlorophenyl)carbamothioyl]piperazine-1-carboxylate;

N-(3,4-dichlorophenyl)-4-(2-pyridyl)piperazine-1-carbothioamide;

N-(3-methoxyphenyl)-4-methyl-piperazine-1-carbothioamide;

N-(3,5-dimethylphenyl)-4-methyl-piperazine-1-carbothioamide;

N-(2,4-dimethylphenyl)-4-methyl-piperazine-1-carbothioamide;

1-tert-butyl-3-(3,4-dichlorophenyl)thiourea;

N-(4-chloro-2,5-dimethoxy-phenyl)-4-methyl-piperazine-1-carbothioamide;

N-(4-anilinophenyl)-4-methyl-piperazine-1-carbothioamide;

1-(3,4-dichlorophenyl)-3-(4-ethylphenyl)thiourea;

1-(3,4-dichlorophenyl)-3-(m-tolyl)thiourea;

N-(3,4-dichlorophenyl)-4-pyrimidin-2-yl-piperazine-1-carbothioamide;

N-(3-chloro-4-fluoro-phenyl)-4-methylsulfonyl-piperazine-1-carbothioamide;

N-(3-chloro-4-methyl-phenyl)-4-ethyl-piperazine-1-carbothioamide;

1-(3-chloro-4-fluoro-phenyl)-3-[4-(diethylamino)phenyl]thiourea and

1-[(3-chlorophenyl)methyl]-1-(2-morpholinoethyl)-3-phenyl-thiourea.

In another embodiment, the method of treatment according to the instant invention includes compound N-(3,4-dichlorophenyl)piperidine-1-carbothioamide.

In yet another embodiment, the method of treatment according to the instant invention includes compound N-(3,4-dichlorophenyl)morpholine-4-carbothioamide.

In yet another embodiment, the mammal being treated is a human. Further, in a particular embodiment, an Arenavirus may be selected from the group consisting of, but not limited to, Junin, Machupo, Guanarito, Sabia, Lassa, Tacaribe, and Pichinde.

Also described herein are pharmaceutical compositions for the treatment of an Arenavirus infection and diseases associated therewith in a mammal, that comprise a therapeutically effective amount of one or more of the compounds of Formula I as described below:

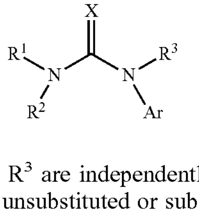

wherein $R^1$, $R^2$ and $R^3$ are independently hydrogen, alkyl, alkenyl, alkynyl, or unsubstituted or substituted cycloalkyl, arylalkyl, aryl, or $R^1$ and $R^2$ together may form a substituted or unsubstituted ring, which may include one or more heteroatoms in the ring;

X is O or S; and

Ar is substituted or unsubstituted aryl or heteroaryl, said cycloalkyl, arylalkyl, and aryl group substituents being one or more radical(s) independently selected from the group consisting of a straight- or branched chain alkyl, alkoxy, alkoxyalkyl, alkoxyalkoxy, halogen, polyfluoroalkyl, polyfluoroalkoxy, carboxy, cyano, nitro, amido, amidoalkyl, carboxamide, alkylthio, alkylsulfinyl, alkylsulfonyl, sulfonamide, and mercapto; and wherein the compound of Formula I is selected from the group consisting of:

N1,N4-diphenylpiperazine-1,4-dicarbothioamide;

N-(4-chlorophenyl)-4-methyl-piperazine-1-carbothioamide;

N-(3,4-dichlorophenyl)-4-phenyl-piperazine-1-carbothioamide;

N-(3-chlorophenyl)-4-methyl-piperazine-1-carbothioamide;

N-(2,4-dichlorophenyl)-4-methyl-piperazine-1-carbothioamide;

4-methyl-N-(m-tolyl)piperazine-1-carbothioamide;

N-(3,4-dichlorophenyl)piperidine-1-carbothioamide;

N-(3,4-dichlorophenyl)morpholine-4-carbothioamide;

4-methyl-N-[3-(trifluoromethyl)phenyl]piperazine-1-carbothioamide;

ethyl 4-[(3,4-dichlorophenyl)carbamothioyl]piperazine-1-carboxylate;

N-(3,4-dichlorophenyl)-4-(2-pyridyl)piperazine-1-carbothioamide;

N-(3-methoxyphenyl)-4-methyl-piperazine-1-carbothioamide;

N-(3,5-dimethylphenyl)-4-methyl-piperazine-1-carbothioamide;

N-(2,4-dimethylphenyl)-4-methyl-piperazine-1-carbothioamide;

1-tert-butyl-3-(3,4-dichlorophenyl)thiourea;

N-(4-chloro-2,5-dimethoxy-phenyl)-4-methyl-piperazine-1-carbothioamide;

N-(4-anilinophenyl)-4-methyl-piperazine-1-carbothioamide;

1-(3,4-dichlorophenyl)-3-(4-ethylphenyl)thiourea;

1-(3,4-dichlorophenyl)-3-(m-tolyl)thiourea;

N-(3,4-dichlorophenyl)-4-pyrimidin-2-yl-piperazine-1-carbothioamide;

N-(3-chloro-4-fluoro-phenyl)-4-methylsulfonyl-piperazine-1-carbothioamide;

N-(3-chloro-4-methyl-phenyl)-4-ethyl-piperazine-1-carbothioamide;

1-(3-chloro-4-fluoro-phenyl)-3-[4-(diethylamino)phenyl] thiourea; and

1-[(3-chlorophenyl)methyl]-1-(2-morpholinoethyl)-3-phenyl-thiourea.

The present invention also provides for a pharmaceutical composition that comprises compound N-(3,4-dichlorophenyl)piperidine-1-carbothioamide.

The present invention also provides for a pharmaceutical composition that comprises compound N-(3,4-dichlorophenyl)morpholine-4-carbothioamide.

Pharmaceutical Formulations of the Compounds

In general, compounds will be administered in a therapeutically-effective amount by any of the accepted modes of administration for these compounds. The compounds can be administered by a variety of routes, including, but not limited to, oral, parenteral (e.g., subcutaneous, subdural, intravenous, intramuscular, intrathecal, intraperitoneal, intracerebral, intraarterial, or intralesional routes of administration), topical, intranasal, localized (e.g., surgical application or surgical suppository), rectal, and pulmonary (e.g., aerosols, inhalation, or powder). Accordingly, these compounds are effective as both injectable and oral compositions. The compounds can be administered continuously by infusion or by bolus injection.

The actual amount of the compound, i.e., the active ingredient, will depend on a number of factors, such as the severity of the disease, i.e., the condition or disease to be treated, age, and relative health of the subject, the potency of the compound used, the route and form of administration, and other factors.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage for use in humans. The dosage of such compounds lies within a range of circulating concentrations that include the $ED_{50}$ with little or no toxicity. The dosage may vary within this range depending upon the dosage form employed and the route of administration utilized. For any compound used, the therapeutically-effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The amount of the pharmaceutical composition administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically-effective dose." Amounts effective for this use will depend on the disease condition being treated as well as by the judgment of the attending clinician depending upon factors such as the severity of the inflammation, the age, weight, and general condition of the patient, and the like.

The compositions administered to a patient are in the form of pharmaceutical compositions described supra. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. It will be understood that use of certain of the foregoing excipients, carriers, or stabilizers will result in the formation of pharmaceutical salts.

The active compound is effective over a wide dosage range and is generally administered in a pharmaceutically- or therapeutically-effective amount. The therapeutic dosage of the compounds will vary according to, for example, the particular use for which the treatment is made, the manner of administration of the compound, the health and condition of the patient, and the judgment of the prescribing physician. For example, for intravenous administration, the dose will typically be in the range of about 0.5 mg to about 100 mg per kilogram body weight. Effective doses can be extrapolated from dose-response curves derived from in vitro or animal model test systems. Typically, the clinician will administer the compound until a dosage is reached that achieves the desired effect.

When employed as pharmaceuticals, the compounds are usually administered in the form of pharmaceutical compositions. Pharmaceutical compositions contain as the active ingredient one or more of the compounds above, associated with one or more pharmaceutically-acceptable carriers or excipients. The excipient employed is typically one suitable for administration to human subjects or other mammals. In making the compositions, the active ingredient is usually mixed with an excipient, diluted by an excipient, or enclosed within a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained, or delayed-release of the active ingredient after administration to the patient by employing procedures known in the art.

The quantity of active compound in the pharmaceutical composition and unit dosage form thereof may be varied or adjusted widely depending upon the particular application, the manner or introduction, the potency of the particular compound, and the desired concentration. The term "unit dosage forms" refers to physically-discrete units suitable as unitary dosages for human subjects and other mammals, each unit containing a predetermined quantity of active material calculated to produce the desired therapeutic effect, in association with a suitable pharmaceutical excipient.

The compound can be formulated for parenteral administration in a suitable inert carrier, such as a sterile physiological saline solution. The dose administered will be determined by route of administration.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost-effective. All of these factors ultimately determine the overall success and usefulness of an intravenous formulation.

Other accessory additives that may be included in pharmaceutical formulations and compounds as follow: solvents: ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer is necessary to maintain the aqueous pH in the range of from about 4 to about 8. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffenalendronate (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

A useful buffer is sodium citrate/citric acid in the range of 5 to 50 mg per ml, sodium citrate to 1 to 15 mg per ml, citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

An intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 2000 mg of the active ingredient.

The tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically-acceptable, aqueous or organic solvents, or mixtures thereof, and powders. The liquid or solid compositions may contain suitable pharmaceutically-acceptable excipients as described supra. Compositions in pharmaceutically-acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered from devices which deliver the formulation in an appropriate manner.

The compounds can be administered in a sustained release form. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or poly(vinyl alcohol)), polylactides (U.S. Pat. No. 3,773,919), copolymers of L-glutamic acid and gamma ethyl-L-glutamate (Sidman et al., *Biopolymers* 22: 547-556, 1983), non-degradable ethylene-vinyl acetate (Langer et ah, supra), degradable lactic acid-glycolic acid copolymers such as the LUPRON DEPOT™ (i.e., injectable microspheres composed of lactic acid-glycolic acid copolymer and leuprolide acetate), and poly-D-(−)-3-hydroxybutyric acid (EP 133,988).

The compounds can be administered in a sustained-release form, for example a depot injection, implant preparation, or osmotic pump, which can be formulated in such a manner as to permit a sustained-release of the active ingredient. Implants for sustained-release formulations are well-known in the art. Implants may be formulated as, including but not limited to, microspheres, slabs, with biodegradable or non-biodegradable polymers. For example, polymers of lactic acid and/or glycolic acid form an erodible polymer that is well-tolerated by the host. The implant is placed in proximity to the site of protein deposits (e.g., the site of formation of amyloid deposits associated with neurodegenerative disorders), so that the local concentration of active agent is increased at that site relative to the rest of the body.

The following formulation examples illustrate pharmaceutical compositions.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/capsule) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/capsule) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium Carboxymethyl starch | 4.5 mg |

-continued

| Ingredient | Quantity (mg/capsule) |
|---|---|
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules, which after mixing, are compressed on a tablet machine to yield tablets each weighing 150 mg.

Formulation Example 5

Capsules, each containing 40 mg of medicament, are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

Formulation Example 6

Suppositories, each containing 25 mg of active ingredient, are made as follows:

| Ingredient | Amount |
|---|---|
| Active Ingredient | 25 mg |
| Saturated fatty acids glycerides | to 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose, are made as follows:

| Ingredient | Amount |
|---|---|
| Active Ingredient | 50.0 mg |
| Xanthan gum | 4.0 mg |
| Sodium carboxymethyl cellose (11%) Microcrystalline cellulose (89%) | 500 mg |
| Sucrose | 1.75 g |

-continued

| Ingredient | Amount |
|---|---|
| Sodium benzoate | 10.0 mg |
| Flavor and color | q.v. |
| Purified water | to 5.0 ml |

The medicament, sucrose, and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Hard gelatin tablets, each containing 15 mg of active ingredient, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
|---|---|
| Active Ingredient | 250.0 mg |
| Isotonic saline | 1000 ml |

Therapeutic compound compositions generally are placed into a container having a sterile access port, for example, an intravenous solution bag or vial having a stopper pierceable by a hypodermic injection needle or similar sharp instrument.

Formulation Example 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

An aerosol formulation may be prepared as follows: A solution of the candidate compound in 0.5% sodium bicarbonate/saline (w/v) at a concentration of 30.0 mg/mL is prepared using the following procedure:

Preparation of 0.5% Sodium Bicarbonate/Saline Stock Solution: 100.0 mL

| Ingredient | Gram/100.0 mL | Final |
|---|---|---|
| Sodium | 0.5 g | 0.5% |
| Saline | q.s. ad 100.0 mL | q.s. ad 100% |

Procedure:

1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

Preparation of 30.0 mg/mL Candidate Compound: 10.0 mL

| Ingredient | Gram/10.0 mL | Final |
|---|---|---|
| Candidate Compound | 0.300 g | 30.0 mg/mL |
| 0.5% Sodium Bicarbonate/ | q.s. ad 10.0 mL | q.s ad 100% |

Procedure:

1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix Transdermal delivery devices ("patches") may also be employed. Such transdermal patches may be used to provide continuous or discontinuous infusion of the compounds in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on-demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid-soluble and amenable to transportation across the blood-brain barrier. Alternatively, the delivery of hydrophilic drugs may be enhanced by intra-arterial infusion of hypertonic solutions which can transiently open the blood-brain barrier.

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka et al., U.S. Pat. Nos. 4,235,871, 4,501,728 and 4,837,028 each of which is incorporated herein by reference.

Pharmaceutical compositions are suitable for use in a variety of drug delivery systems. Suitable formulations for use in the present invention are found in *Remington's Pharmaceutical Sciences*, Mace Publishing Company, Philadelphia, Pa., 17th ed. (1985).

The provided compounds and pharmaceutical compositions show biological activity in treating and preventing viral infections and associated diseases, and, accordingly, have utility in treating viral infections and associated diseases, such as Hemorrhagic fever viruses, in mammals including humans.

Hemorrhagic fever viruses (HFVs) are RNA viruses that cause a variety of disease syndromes with similar clinical characteristics. HFVs that are of concern as potential biological weapons include but are not limited to: Arenaviridae (Junin, Machupo, Guanarito, Sabia, Lassa, and LCMV), Filoviridae (Ebola and Marburg viruses), Flaviviridae (yellow fever, Omsk hemorrhagic fever and Kyasanur Forest disease viruses), and Bunyaviridae (Rift Valley fever). The naturally-occurring arenaviruses and potential engineered arenaviruses are included in the Category A Pathogen list according to the Centers for Disease Control and Prevention as being among those agents that have greatest potential for mass casualties.

Risk factors include: travel to Africa or Asia, handling of animal carcasses, contact with infected animals or people, and/or arthropod bites. Arenaviruses are highly infectious after direct contact with infected blood and/or bodily secretions. Humans usually become infected through contact with infected rodents, the bite of an infected arthropod, direct contact with animal carcasses, inhalation of infectious rodent excreta and/or injection of food contaminated with rodent excreta. The Tacaribe virus has been associated with bats. Airborne transmission of hemorrhagic fever is another mode, but somewhat less common. Person-to-person contact may also occur in some cases.

All of the hemorrhagic fevers exhibit similar clinical symptoms. However, in general the clinical manifestations are non-specific and variable. The incubation period is approximately 7-14 days. The onset is gradual with fever and malaise, tachypnea, relative bradycardia, hypotension, circulatory shock, conjeunctival injection, pharyngitis, lymphadenopathy, encephalitis, myalgia, back pain, headache and dizziness, as well as hyperesthesia of the skin. Some infected patients may not develop hemorrhagic manifestations.

Methods of diagnosis at specialized laboratories include antigen detection by antigen-capture enzyme-linked immunosorbent assay (ELISA), IgM antibody detection by antibody-capture enzyme-linked immunosorbent assay, reverse transcriptase polymerase chain reaction (RT-PCR), and viral isolation. Antigen detection (by enzyme-linked immunosorbent assay) and reverse transcriptase polymerase chain reaction are the most useful diagnostic techniques in the acute clinical setting. Viral isolation is of limited value because it requires a biosafety level 4 (BSL-4) laboratory.

In vitro cell-based studies have been performed that demonstrate the usefulness of compounds described herein as antiviral agents. For example, antiviral activity of representative compounds was evaluated in assays that measure the ability of compounds to protect cells from virus-induced CPE. Cells that will support growth of the particular arena virus strain are seeded into 96-well tissue culture treated plates and then infected with an amount of the appropriate arena virus strain that results in complete CPE in about 7 days. Various dilutions of inhibitory compound(s) are added and the plates are incubated at the appropriate temperature for optimal virus growth. At the end of the incubation period, cells are fixed with glutaraldehyde and stained with crystal violet. Cell protection is measured spectrophotometrically at $OD_{570}$ nm. The interpolated compound dilution that results in 50% protection of the cell monolayer from virus-induced CPE is calculated and reported as the 50% effective concentration or $EC_{50}$. Antiviral activity of representative compounds described herein occurred at drug concentrations that had no demonstrable effect on cell growth, indicating that the compounds were working specifically by an antiviral mechanism.

The following examples illustrate suitable methods of synthesis of representative compounds described herein. However, the methods of synthesis are intended to illustrate and not to limit the invention to those exemplified below. The starting materials for preparing the antiviral compounds described herein are either commercially available or can be conveniently prepared according to one of the examples set forth below or otherwise using known chemistry procedures.

Example 1

General Synthetic Procedure

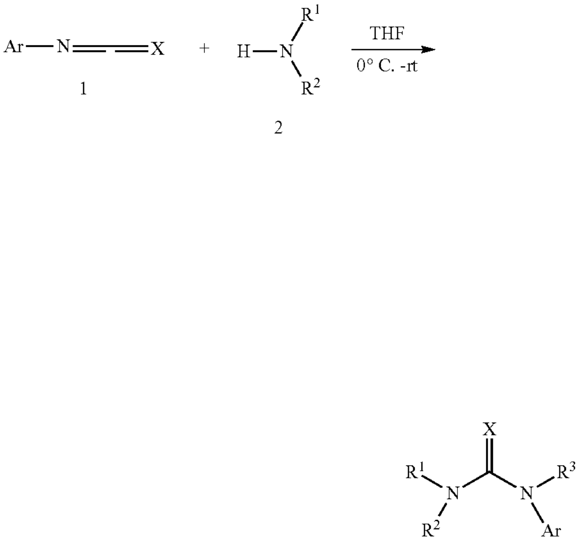

X = S, O
3

Compound 1 (phenyl isothiocyanate or phenyl isocyanate, 11.8 mMol) is dissolved in THF (20 mL) with ice-water cooling under $N_2$. To the solution is added compound 2 (11.8 mMol) in THF (5 mL) drop by drop over 30 minutes. White solid precipitates in 5 minutes. The ice-water bath is removed and the suspension is further stirred at room temperature for 1 hr and then left standing in refrigerator for 3 hrs. Filtration of the mixture gives a white solid 3. The mother liquid is concentrated to 10 mL and then is left standing at rt overnight. Filtration gives a white crystalline solid (3). The combined solid is dried and weighted.

Example 2

Preparation of 4-methyl-piperazine-1-carbothioic acid (3,4-dichlorophenyl)-amide

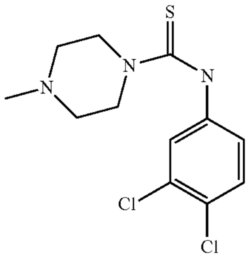 [SMILES: CN1CCN(C(=S)Nc2ccc(Cl)c(Cl)c2)CC1]

The compound is prepared according to the General Synthetic Procedure in Example 1 in 74%. $^1H$ NMR in DMSO-$d_6$: δ 9.45 (s, 1H), 7.62 (d, 1H), 7.53 (d, 1H), 7.32 (dd, 1H), 3.88 (t, 4H), 2.37 (t, 4H), 2.21 (s, 3H).

Example 3

Inhibition of Arenaviral Replication

The ability of the compounds of described herein to inhibit Arenavirus was established by the following experimental procedure:

(a) Preparation of Virus Stock:

Virus stocks of arenavirus were prepared in Vero cells infected at low multiplicity (0.01 plaque forming units (PFU)/cell) and harvested when cytopathic effects were complete. The samples were frozen and thawed and then sonicated to release cell-associated virus. The cell debris was removed by low-speed centrifugation, and the resulting virus suspension was stored in 1 mL aliquots at −80° C. The PFU/mL of the virus suspension was quantified by standard plaque assay on Vero cells.

(b) Arena CPE: Assay:

To determine the amount of arenavirus stock required to produce complete CPE in 7 days, Vero cell monolayers were seeded on to 96-well plates and infected with 2-fold serial dilutions of the arenavirus stock. At 7 days post-infection, the cultures were fixed with 5% glutaraldehyde and stained with 0.1% crystal violet. Virus-induced CPE was quantified spectrophotometrically at $OD_{570}$. From this analysis, a 1:1000 dilution of Tacaribe virus (TRVL 11573) stock was chosen for use in the HTS assay.

The results of these experiments indicated that the 96-well assay format was robust and reproducible. The S/N ratio (ratio of signal of cell control wells (signal) to virus control wells (noise)) was 9.2±1.8. The well-to-well and assay-to-assay variability was less than 20%. Based on this analysis, the 1:1000 dilution of Tacaribe virus was chosen for use in the assay.

(c) Compound Testing:

Representative compounds described herein were tested in the Tacaribe (TRVL 11573) virus CPE assay.

Compounds were dissolved in DMSO and diluted in medium such that the final concentration in each well was 5 μM compound and 0.5% DMSO. The compounds are added robotically to the culture medium. Following compound addition, the cultures were infected with Tacaribe virus. After 7 days, plates were processed and CPE quantified as described.

Representative compounds described herein inhibited Tacaribe (TRVL 11573) virus-induced CPE by greater than 50% at the test concentration (5 μM). Selected compounds were further evaluated for potency ($EC_{50}$) in the CPE assay and cytotoxicity ($CC_{50}$) in an MTT assay. The MTT assay measures mitochondrial dehydrogenase activity in dividing cells. This method detects the in situ reduction of (3-(4,5-dimethylthiazol-2-yl)-5-(3-carboxymethoxyphenyl)-2-(4-sulfophenyl-)-2H-tetrazolium) using an electron coupling reagent (phenazine methosulfate) to produce an insoluble formazan. The absorbance of the formazan at 490 nm can be measured directly from 96-well assay plates following solubilization of the formazan in 50% ethanol. The quantity of formazan product is directly proportional to the number of living cells in culture.

The inhibitory concentration 50% ($EC_{50}$) values were determined from a plot of the compound inhibitory activity following the Tacaribe (TRVL 11573) CPE assay across eight compound concentrations (50, 16, 5, 1.6, 0.5, 0.16, 0.05 and 0.016 μM). All determinations were performed in duplicate. $EC_{50}$ values were calculated by comparing compound-treated and compound-untreated cells using a computer program. The $EC_{50}$ value of the representative compound (the compound in Example 2) in the CPE assay is 140 nM. This antiviral is active at non-toxic concentrations.

Spectrum and Specificity of Activity of Compounds

Several additional CPE inhibition assays, similar to above, are utilized to identify a spectrum of activity of compounds of the compounds described herein within the arena genus. The $EC_{50}$ was calculated as the compound concentration required to reduce virus plaque numbers by 50%. Under BSL 4 conditions at USAMRIID the plaque reduction assays (with Lassa, Machupo, Guanarito, and Junín viruses) were performed as follows: 200 PFU of each virus was used to infect Vero cells. After virus adsorption, cell monolayers were rinsed and overlaid with complete medium containing 1% agarose and either lacking test compound or with different concentrations ranging from 15 μM to 0.05 μM. After 5 days incubation at 37° C., the monolayers were stained with neutral red and the numbers of plaques were counted.

The specificity of representative compounds for arena virus inhibition is reflected in the fact that they do not inhibit the replication of unrelated viruses, including Pichinde virus, Rift Valley fever virus (strain MP12), respiratory syncytial virus and cytomegalovirus.

Example 4

Approximately 400,000 compounds from an established compound library were tested in this assay. Assay plates were set up as follows. For the HTS CPE assay, Vero cells were plated at 80% confluency on 96-well plates. Test compounds (80 per plate) from the library were added to wells at a final concentration of 5 μM. Tacaribe virus was then added at a virus dilution that would result in 90% CPE after 7 days (pre-determined as a 1000-fold dilution of the virus stock; multiplicity of infection [MOI] approximately 0.001). Plates were incubated at 37° C. and 5% $CO_2$ for 7 days, then fixed with 5% glutaraldehyde and stained with 0.1% crystal violet. The extent of virus CPE was quantified spectrometrically at $OD_{570}$ using an Envision Microplate Reader. The inhibitory activity of each compound was calculated by subtracting from the $OD_{570}$ of test compound well from the average $OD_{570}$ of virus-infected cell wells, then dividing by the average $OD_{570}$ of mock-infected cell wells. The result represents the percent protection against Tacaribe virus CPE activity conferred by each compound. "Hits' in this assay were defined as compound that inhibited virus-induced CPE by greater than 50% at the test concentration (5 μM). Of the approximately 400,000 compounds screened in the Tacaribe virus HTS campaign, 2,347 hits were identified (0.58% hit rate).

Quality hits are defined as inhibitor compounds (hits) that exhibit acceptable chemical structures, antiviral potency and selectivity, and spectrum of antiviral activity. Specifically, compounds identified as hits in HTS assays (described above) were evaluated against four criteria: i) chemical tractability, ii) inhibitory potency, iii) inhibitory selectivity and, iv) antiviral specificity. Based on the HTS parameters, all hits have $EC_{50}$ values <5 μM. The chemical structures of compounds that met this initial criterion were visually examined for chemical tractability. A chemically tractable compound is defined as an entity that is synthetically accessible using reasonable chemical methodology, and which possesses chemically stable functionalities and (potential) drug-like qualities. Hits that passed this medicinal chemistry filter were evaluated for their inhibitory potency. $EC_{50}$ values were determined from a plot of the compound inhibitory activity, typically across eight compound concentrations (50, 16, 5, 1.6, 0.5, 0.16, 0.05 and 0.016 μM). To assess whether the hit is a selective inhibitor, the effect on cellular functions was determined using a standard cell proliferation assay. A 50% cytotoxicity concentration ($CC_{50}$) was determined using a tetrazolium-based colorimetric method, which measures the in situ reduction of 3-(4,5-dimethylthiazol-2-yl)-2,5-diphenyl tetrazolium bromide (MTT) to insoluble blue formazan crystals by mitochondrial enzymes in metabolically active cells. Solubilized crystals were quantified spectrometrically. Using the $EC_{50}$ and $CC_{50}$ values, a Selective Index (SI) was calculated ($SI=CC_{50}/EC_{50}$). Hits with SI values of at least 10 were considered further. The specificity of the antiviral activity exhibited by hit compounds was determined by testing the compounds against a number of related and unrelated viruses. Compounds are tested against a variety of unrelated DNA (HSV, CMV, vaccinia virus) and RNA (RSV, rotavirus, Rift Valley fever, Ebola virus, Ebola GP-pseudotype, Lassa GP-pseudotype, HIV env-pseudotype) viruses. Compounds described in Table 1 and Table 2 below herein are very selective against the selected original target virus and inactive against unrelated viruses.

Compounds 7 and 8 listed in Table 2 below, namely N-(3,4-dichlorophenyl)piperidine-1-carbothioamide and N-(3,4-dichlorophenyl)morpholine-4-carbothioamide, are very potent inhibitors of an Arenavirus infection mediated by but not limited to Tacaribe ($EC_{50}$=<1 μM), Machupo ($EC_{50}$=<1 μM), and Pichinde ($EC_{50}$=<1 μM) as compared to nonrelated VSV ($EC_{50>}$25 μM)

TABLE 1
| Compound number | $EC_{50}/CC_{50}$ µM Tacaribe | $EC_{50}/CC_{50}$ µM Candid 1 | $EC_{50}$ (µM) Category A NWA | Structure |
|---|---|---|---|---|
| 313761 | 0.14/50 | 0.26/50 | Machupo: 0.3<br>Guanarito: 0.15 | 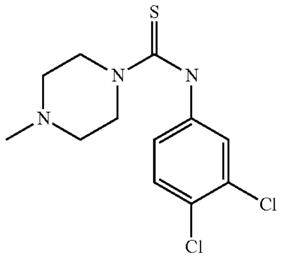 [SMILES: CN1CCN(C(=S)Nc2ccc(Cl)c(Cl)c2)CC1] |
| 280611 | 0.06/25 | 0.05/25 | Not tested | 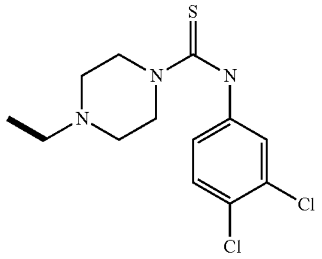 |
| 20013 | >50/>50 | >50/>50 | Not tested | 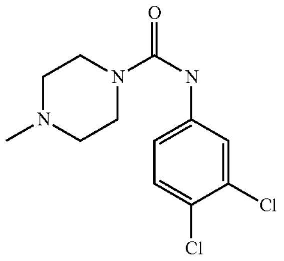 [SMILES: CN1CCN(C(=O)Nc2ccc(Cl)c(Cl)c2)CC1] |
TABLE 2
| Compound | Structure | IUPAC Name | EC50s (µM) vs. pseudotypes | | | |
|---|---|---|---|---|---|---|
| | | | Tacaribe | Machupo | Pichinde | VSV |
| 1 | 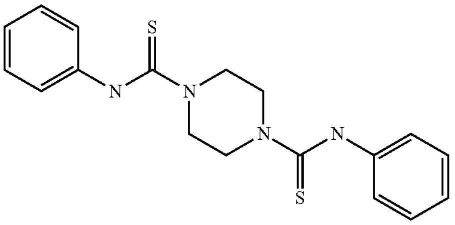 [SMILES: S=C(Nc1ccccc1)N1CCN(C(=S)Nc2ccccc2)CC1] | N1,N4-diphenylpiperazine-1,4-dicarbothioamide | 1.81 | 2.4 | 4.2 | >25 |
| 2 | 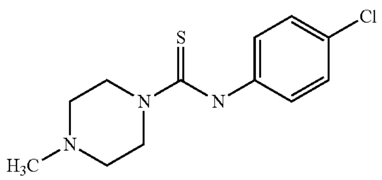 [SMILES: CN1CCN(C(=S)Nc2ccc(Cl)cc2)CC1] | N-(4-chlorophenyl)-4-methyl-piperazine-1-carbothioamide | 0.51 | 0.54 | 6.8 | >25 |

TABLE 2-continued

| Compound | Structure | IUPAC Name | EC50s (μM) vs. pseudotypes Tacaribe | Machupo | Pichinde | VSV |
|---|---|---|---|---|---|---|
| 3 | 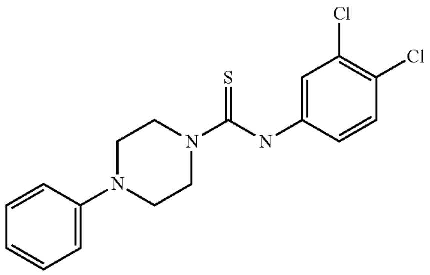 [SMILES: S=C(Nc1ccc(Cl)c(Cl)c1)N1CCN(c2ccccc2)CC1] | N-(3,4-dichlorophenyl)-4-phenyl-piperazine-1-carbothioamide | 0.20 | 0.32 | 1.87 | >25 |
| 4 | 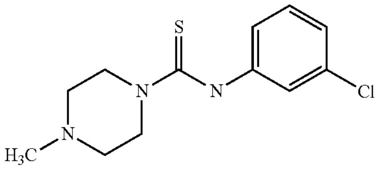 [SMILES: CN1CCN(C(=S)Nc2cccc(Cl)c2)CC1] | N-(3-chlorophenyl)-4-methyl-piperazine-1-carbothioamide | 0.84 | 0.58 | 4.1 | >25 |
| 5 | 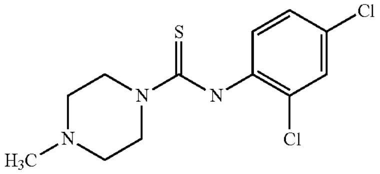 [SMILES: CN1CCN(C(=S)Nc2ccc(Cl)cc2Cl)CC1] | N-(2,4-dichlorophenyl)-4-methyl-piperazine-1-carbothioamide | 0.94 | 0.56 | 2.1 | >25 |
| 6 | 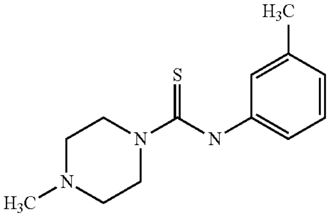 [SMILES: Cc1cccc(NC(=S)N2CCN(C)CC2)c1] | 4-methyl-N-(m-tolyl)piperazine-1-carbothioamide | 2.1 | 3.8 | 16.4 | >25 |
| 7 | 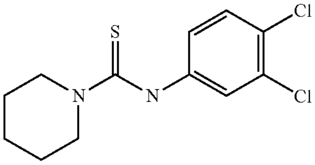 [SMILES: S=C(Nc1ccc(Cl)c(Cl)c1)N1CCCCC1] | N-(3,4-dichlorophenyl)piperidine-1-carbothioamide | 0.109 | 0.28 | 0.98 | >25 |
| 8 | 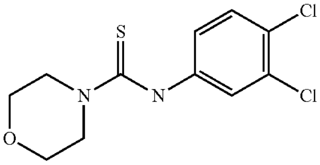 [SMILES: S=C(Nc1ccc(Cl)c(Cl)c1)N1CCOCC1] | N-(3,4-dichlorophenyl)morpholine-4-carbothioamide | 0.178 | 0.48 | 1.02 | >25 |
| 9 | 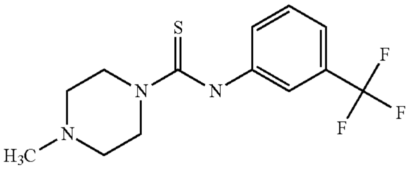 [SMILES: CN1CCN(C(=S)Nc2cccc(C(F)(F)F)c2)CC1] | 4-methyl-N-[3-(trifluoromethyl)phenyl]piperazine-1-carbothioamide | 0.30 | 0.32 | 1.38 | >25 |

TABLE 2-continued

| Com-pound | Structure | IUPAC Name | EC50s (μM) vs. pseudotypes Tacaribe | Machupo | Pichinde | VSV |
|---|---|---|---|---|---|---|
| 10 | 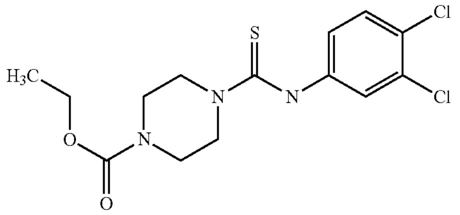 [SMILES: CCOC(=O)N1CCN(C(=S)Nc2ccc(Cl)c(Cl)c2)CC1] | ethyl 4-[(3,4-dichloro-phenyl)carbamothioyl]piper-azine-1-carboxylate | 0.174 | 0.22 | 1.16 | >25 |
| 11 | 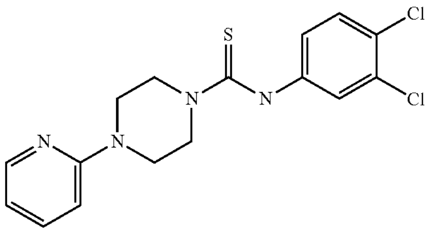 [SMILES: S=C(Nc1ccc(Cl)c(Cl)c1)N1CCN(c2ccccn2)CC1] | N-(3,4-dichlorophenyl)-4-(2-pyridyl)piperazine-1-carbothioamide | 0.29 | 0.44 | 1.54 | >25 |
| 12 | 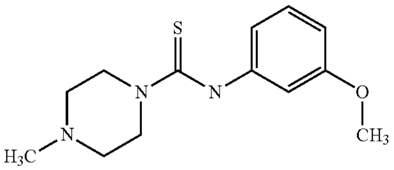 | N-(3-methoxyphenyl)-4-methyl-piperazine-1-carbothioamide | 7.1 | 5.7 | 18.9 | >25 |
| 13 | 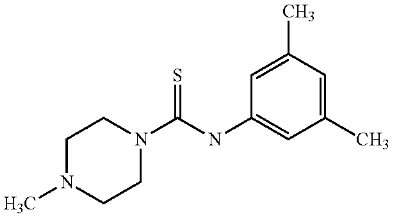 | N-(3,5-dimethylphenyl)-4-methyl-piperazine-1-carbothioamide | 0.94 | 3.3 | 6.7 | >25 |
| 14 | 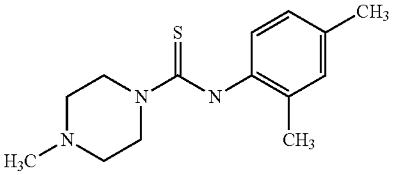 | N-(2,4-dimethylphenyl)-4-methyl-piperazine-1-carbothioamide | 3.2 | 6.1 | 22 | >25 |
| 15 | 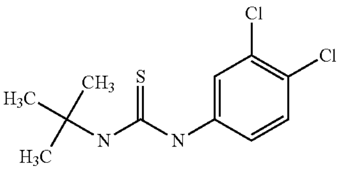 [SMILES: CC(C)(C)NC(=S)Nc1ccc(Cl)c(Cl)c1] | 1-tert-butyl-3-(3,4-dichlorophenyl)thiourea | 3.5 | 5.7 | 16.0 | >25 |
| 16 | 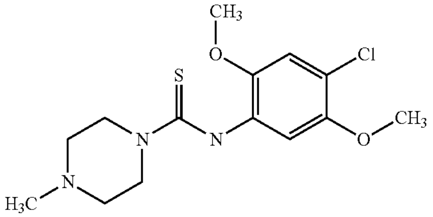 | N-(4-chloro-2,5-dimethoxy-phenyl)-4-methyl-piperazine-1-carbothioamide | 6.6 | 10.7 | 13.2 | >25 |

TABLE 2-continued

| Compound | Structure | IUPAC Name | EC50s (μM) vs. pseudotypes Tacaribe | Machupo | Pichinde | VSV |
|---|---|---|---|---|---|---|
| 17 | 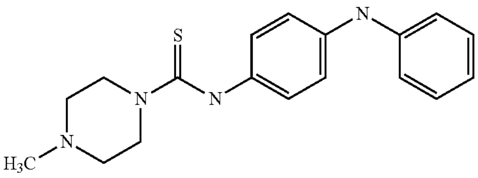 [SMILES: CN1CCN(C(=S)Nc2ccc(Nc3ccccc3)cc2)CC1] | N-(4-anilinophenyl)-4-methyl-piperazine-1-carbothioamide | 3.0 | 3.9 | 12.0 | >25 |
| 18 | 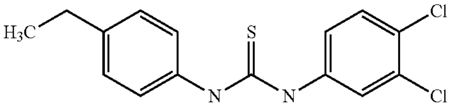 [SMILES: CCc1ccc(NC(=S)Nc2ccc(Cl)c(Cl)c2)cc1] | 1-(3,4-dichlorophenyl)-3-(4-ethylphenyl)thiourea | 0.44 | 0.81 | 2.4 | 7.9 |
| 19 | 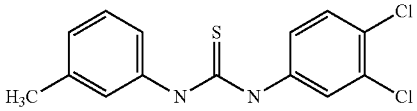 [SMILES: Cc1cccc(NC(=S)Nc2ccc(Cl)c(Cl)c2)c1] | 1-(3,4-dichlorophenyl)-3-(m-tolyl)thiourea | 0.57 | 1.21 | 3.8 | 22 |
| 20 | 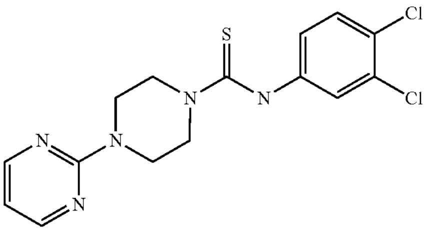 [SMILES: S=C(Nc1ccc(Cl)c(Cl)c1)N1CCN(c2ncccn2)CC1] | N-(3,4-dichlorophenyl)-4-pyrimidin-2-yl-piperazine-1-carbothioamide | 0.21 | 0.28 | 1.65 | >25 |
| 21 | 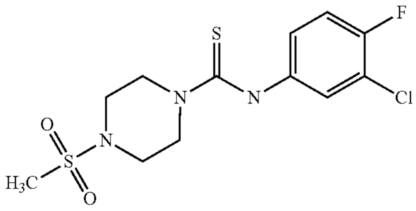 [SMILES: CS(=O)(=O)N1CCN(C(=S)Nc2ccc(F)c(Cl)c2)CC1] | N-(3-chloro-4-fluoro-phenyl)-4-methylsulfonyl-piperazine-1-carbothioamide | 0.63 | 0.85 | 3.2 | >25 |
| 22 | 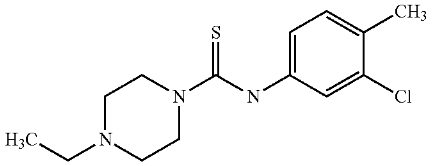 [SMILES: CCN1CCN(C(=S)Nc2ccc(C)c(Cl)c2)CC1] | N-(3-chloro-4-methyl-phenyl)-4-ethyl-piperazine-1-carbothioamide | 0.29 | 0.36 | 1.60 | >25 |
| 23 | 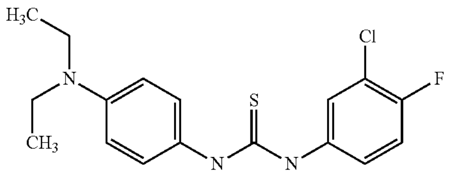 [SMILES: CCN(CC)c1ccc(NC(=S)Nc2ccc(F)c(Cl)c2)cc1] | 1-(3-chloro-4-fluoro-phenyl)-3-[4-(diethyl-amino)phenyl]thiourea | 3.9 | 5.4 | 21 | >25 |
| 24 | 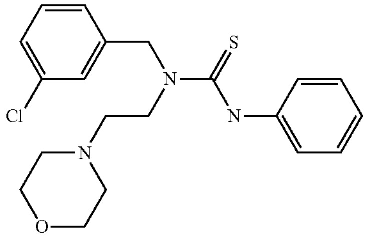 [SMILES: S=C(Nc1ccccc1)N(CCN1CCOCC1)Cc1cccc(Cl)c1] | 1-[(3-chlorophenyl)methyl]-1-(2-morpholinoethyl)-3-phenyl-thiourea | 2.9 | 3.1 | 19.2 | >25 |

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What we claim is:

1. A method for treatment of an Arenavirus infection comprising administering in a therapeutically effective amount to a mammal in need thereof, a compound selected from the group consisting of:

N1,N4-diphenylpiperazine-1,4-dicarbothioamide;
N-(4-chlorophenyl)-4-methyl-piperazine-1-carbothioamide;
N-(3,4-dichlorophenyl)-4-phenyl-piperazine-1-carbothioamide;
N-(3-chlorophenyl)-4-methyl-piperazine-1-carbothioamide;
N-(2,4-dichlorophenyl)-4-methyl-piperazine-1-carbothioamide;
4-methyl-N-(m-tolyl)piperazine-1-carbothioamide;
N-(3,4-dichlorophenyl)piperidine-1-carbothioamide;
N-(3,4-dichlorophenyl)morpholine-4-carbothioamide;
4-methyl-N-[3-(trifluoromethyl)phenyl]piperazine-1-carbothioamide;
ethyl 4-[(3,4-dichlorophenyl)carbamothioyl]piperazine-1-carboxylate;
N-(3,4-dichlorophenyl)-4-(2-pyridyl)piperazine-1-carbothioamide;
N-(3-methoxyphenyl)-4-methyl-piperazine-1-carbothioamide;
N-(3,5-dimethylphenyl)-4-methyl-piperazine-1-carbothioamide;
N-(2,4-dimethylphenyl)-4-methyl-piperazine-1-carbothioamide;
1-tert-butyl-3-(3,4-dichlorophenyl)thiourea;
N-(4-chloro-2,5-dimethoxy-phenyl)-4-methyl-piperazine-1-carbothioamide;
N-(4-anilinophenyl)-4-methyl-piperazine-1-carbothioamide;
1-(3,4-dichlorophenyl)-3-(4-ethylphenyl)thiourea;
1-(3,4-dichlorophenyl)-3-(m-tolyl)thiourea;
N-(3,4-dichlorophenyl)-4-pyrimidin-2-yl-piperazine-1-carbothioamide;
N-(3-chloro-4-fluoro-phenyl)-4-methylsulfonyl-piperazine-1-carbothioamide;
N-(3-chloro-4-methyl-phenyl)-4-ethyl-piperazine-1-carbothioamide;
1-(3-chloro-4-fluoro-phenyl)-3-[4-(diethylamino)phenyl]thiourea and
1-[(3-chlorophenyl)methyl]-1-(2-morpholinoethyl)-3-phenyl-thiourea.

2. The method of claim 1, wherein the compound of Formula I is N-(3,4-dichlorophenyl)piperidine-1-carbothioamide.

3. The method of claim 1, wherein the compound of Formula I is N-(3,4-dichlorophenyl)morpholine-4-carbothioamide.

4. The method of claim 1, wherein the mammal is a human.

5. The method of claim 1, wherein an Arenavirus is selected from the group consisting of Junin, Machupo, Tacaribe, Guanarito, Machupo, Pichinde and Lassa.

6. The method of claim 1, further comprising administering to the subject an additional antiviral agent selected from the group consisting of zidovudine, acyclovir, ganciclovir, vidarabidine, idoxuridine, trifluridine, foscarnet, interferon, amantadine, rimantadine, and ribavirin.

* * * * *